United States Patent [19]

Opplt

[11] Patent Number: 5,387,325
[45] Date of Patent: Feb. 7, 1995

[54] DISCONTINUOUS AND NONSEQUENTIAL POLYMERIC GEL SYSTEMS FOR SEPARATION OF MACROMOLECULES

[76] Inventor: Jan J. Opplt, 17364 Falling Water Rd., Strongsville, Ohio 44136

[21] Appl. No.: 74,847
[22] PCT Filed: Dec. 13, 1991
[86] PCT No.: PCT/US91/09348
§ 371 Date: Jun. 9, 1993
§ 102(e) Date: Jun. 9, 1993
[87] PCT Pub. No.: WO92/10277
PCT Pub. Date: Jun. 25, 1992

Related U.S. Application Data

[63] Continuation-in-part of Ser. No. 627,054, Dec. 13, 1990, abandoned.

[51] Int. Cl.$^6$ ............................................. B01D 61/46
[52] U.S. Cl. ............................... 204/299 R; 204/182.3
[58] Field of Search ..................... 204/299 R, 182.3; 252/315.1

[56] References Cited

U.S. PATENT DOCUMENTS

| | | | |
|---|---|---|---|
| 3,384,564 | 5/1968 | Ornstein et al. | 204/180 |
| 4,189,370 | 2/1980 | Boschetti | 204/299 R |
| 4,306,956 | 12/1981 | de Castro et al. | 204/180 |
| 4,319,975 | 3/1982 | Cook | 204/180 |
| 4,699,705 | 10/1987 | Ogawa et al. | 204/299 |
| 5,078,853 | 1/1992 | Manning et al. | 204/299 |

FOREIGN PATENT DOCUMENTS 173858 12/1987 Japan.
263548 4/1988 Japan.

OTHER PUBLICATIONS

B. Gahhe, R. K. Juneja and J. Grolmus, "Horizontal polyacrylamide gradient gel electrophoresis for the simultaneous phenotyping of transferrin, post-transferrin, albumin and post-albumin in the blood plasma of cattle." Dept. of Animal Breeding, Swedish Univ. of Agricultural Sciences, Animal Blood Groups Biochem, Genet. 8 (1977) pp. 127-137.

J. B. Ubbink, W. J. Serfontein and L. S. deVillers, "The Direct quantification in whole serum of HDL subfractions.", Dept. of Chemical Pathology, Univ. of Pretoria, Clinica Chimica Acta 125, (1982) (no month) pp. 165-175.

V. Atger, D. Malon, M. Claude Bertiere, F. N'Diaye and A. Girard-Globa, "Cholesterol Distribution Between High-Density-Lipoprotein Subfractions $HDL_2$ and $HDL_3$ Determined in Serum by Discontinuous Gradient Gel Electrophoresis", Clinical Chemistry, vol. 37, No. 7, 1991, (no month) pp. 1149-1152.

D. Roche, V. Atger, N. T. LeQuang, A. Girard and O. G. Ekinkjian, "Polyacrylamide Gel Electrophoresis in Quantification of High-Density Lipoprotein Cholesterol", Clinical Chemistry, vol. 31, No. 11, 1985, pp. 1893-1895.

Allen, Ph.D., Pharmazeutisches Institut der FU,D-1 Berlin 33, Konigin-Luise-Strasse 2-4, Germany, "Electrophoretic Separation of Pre-Stained Lipoproteins on Polyacrylamide Gel Slabs and their Relationship to Other Plasma Proteins". Oct. 6-7, 1972.

Primary Examiner—John Niebling
Assistant Examiner—Edna Wong
Attorney, Agent, or Firm—Fay, Sharpe, Beall, Fagan, Minnich & McKee

[57] ABSTRACT

This invention relates to the formation and use of a variable, multilayer system of discrete, discontinuous and nonsequential molecular sieves, comprising of agarose-acrylic gels of distinct composition. Each of the individual gel-layers of the system is designed according to partition and/or retardation coefficients for specific retention and therefore selective separation of selected molecules of different molecular sizes. The unique multilayer composite acrylic gel system of this invention makes it possible to separate micro- and macromolecules which differ in molecular weights by millions of daltons. So isolated any physically defined molecular groups are superiorly suitable for further chemical, physico-chemical or biological characterization.

1 Claim, 3 Drawing Sheets

| | A | B | C | D | E | F | G | H | I |
|---|---|---|---|---|---|---|---|---|---|
| 0 | | | | | | | | | |
| 1 | 1% | 1% | 1% | 2% | 1.5% | 1.5% | 1.0% | 1.0% | 1.0% |
| 2 | 2% | 2% | 2.2% | 2.5% | | 2.0% | 2.0% | 2.0% | 2.0% |
| 3 | 3% | 3% | 2.4% | 3.0% | | 2.5% | 2.5% | 2.5% | 2.5% |
| 4 | 4% | | 2.6% | 3.2% | 3.0% | 3.0% | | 3.0% | 3.0% |
| 5 | 5% | | 2.8% | 3.4% | 3.3% | 3.2% | | 3.3% | 3.2% |
| 6 | 6% | 4% | 3% | 3.6% | 3.6% | 3.5% | | 3.6% | 3.5% |
| 7 | 7% | 5% | | 3.8% | 3.9% | 3.8% | | 3.9% | |
| 8 | 8% | | | | | 4.6% | 4.8% | | 4.8% |
| 9 | 9% | | 4% | | | 5.8% | 5.8% | | 5.8% |
| 10 | 10% | 6% | 5% | | | 6.2% | 6.2% | | 6.2% |
| 11 | 11% | 7% | 7% | 6.2% | 5.8% | 6.8% | 6.8% | | 6.8% |
| 12 | 12% | 8% | 7.5% | 6.8% | 6.2% | 7.2% | 7.2% | | 7.2% |
| 13 | 13% | 9% | 8.0% | 7.2% | 6.8% | 7.6% | 7.6% | | 7.6% |
| 14 | 14% | 10% | 9.0% | 7.6% | 7.2% | 7.8% | 7.8% | | 7.8% |

| 0 | ☗ | ☗ | ☗ | ☗ | ☗ | ☗ | ☗ | ☗ | ☗ |
|---|---|---|---|---|---|---|---|---|---|
| 1 | 1% | 1% | 1% | 2% | 1.5% | 1.5% | 1.0% | 1.5% | 1.0% |
| 2 | 2% | 2% | 2.2% | 2.5% | | 2.0% | 2.0% | 2.0% | 2.0% |
| 3 | 3% | 3% | 2.4% | 3.0% | | 2.5% | 2.5% | 2.5% | 2.5% |
| 4 | 4% | | 2.6% | 3.2% | 3.0% | 3.0% | | 3.0% | 3.0% |
| 5 | 5% | | 2.8% | 3.4% | 3.3% | 3.2% | | 3.3% | 3.2% |
| 6 | 6% | 4% | 3% | 3.6% | 3.6% | 3.5% | | 3.6% | 3.5% |
| 7 | 7% | 5% | | 3.8% | 3.9% | 3.8% | | 3.9% | |
| 8 | 8% | | | | | 4.8% | 4.8% | 4.6% | 4.8% |
| 9 | 9% | | 4% | | | 5.8% | 5.8% | | 5.8% |
| 10 | 10% | 6% | 5% | | | 6.2% | 6.2% | | 6.2% |
| 11 | 11% | 7% | 7% | 6.2% | 5.8% | 6.8% | 6.8% | | 6.8% |
| 12 | 12% | 8% | 7.5% | 6.8% | 6.2% | 7.2% | 7.2% | | 7.2% |
| 13 | 13% | 9% | 8.0% | 7.2% | 6.8% | 7.6% | 7.6% | | 7.6% |
| 14 | 14% | 10% | 9.0% | 7.6% | 7.2% | 7.8% | 7.8% | | 7.8% |

DISCONTINUOUS AND NONSEQUENTIAL POLYMERIC GEL SYSTEMS FOR SEPARATION OF MACROMOLECULES

This is a continuation-in-part of U.S. patent application Ser. No. 07/627,054, filed Dec. 13, 1990, now abandoned.

BACKGROUND OF THE INVENTION

1. Field of the Invention

This invention relates generally to methods and a system for the separation and resolution of molecular components, including synthetic, organic or biologic particles, from a mixture of such components. More particularly, the invention pertains to a multilayer molecular filtration system comprised of discontinuous and nonsequential, gelous, semifluid or fluid, chromatographic or electrophoretic mediae placed on or inside or around different and presently known and used mechanical vectors, facilitating a movement of polar particles with various molecular characteristics and related methods thereof.

2. Description of Related Art

The use of sieving gels for the separation of organical and/or biological particles is well-known and used in the electrophoresis art from mid-fifties of this century. However, the presently known methods, based on sieving effects demonstrated throughout the years, have serious disadvantages. The most apparent is the inability to separate, satisfactorily, the high and very high molecular particles, e.g., molecular weights greater than 650,000 daltons.

The sieving gels which are most often used for analytical and scientific purposes include the following: cellulose acetate, starch gels, agar-gels, agarose-gels, gels of agarose derivatives, polyacrylamide gels, gradient polyacrylamide gels of different gradients (from 2% to 27% of PAA and 4% to 30% of PAA), pore gradient polyacrylamide gels, mixture of, or combinations of polyacrylamide gels and different derivatives of agarose, as well as any of the above gels with addition of protein-complexes-forming variants (SDS), urea, or emulators (TRITONS), or glass adhesives, etc.

All the above-mentioned gels and combinations thereof are known to be used only in continuous forms (e.g., nongradient mediae), or continuous gradients (e.g., gradient mediae). For example, the most often employed gelous mediae are the agarose-gels. Although gels of different concentrations of purified agarose are utilized for specific purposes (e.g., 1%, 1½%, 2%, 2½%, etc.), all are known as "continuous" gels. In comparison, the "gradient" gels comprise gels (usually polyacrylamidic) of increasing concentrations of acrylamide monomer, as shown by the formula where T equals the percent of monomers concentration:

$$\% T = \frac{g\ ACRYL + g\ BIS}{100\ ml\ gel} \times 100$$

These gels are known to be used in different ranges of their gradients (for instance from 3–7%, or 2–5%, or 2–16%, or 2–27%), but these gradients are known to be always sequentially assorted (e.g., in 3–4–5–6–7%, or 2–3–4–5%, or in 2–3–4–5–6–7–8–9–10–11–12–13–14–15–16% fashion, etc.).

It is noted that the literature discloses only few devices of similar arrangement of two electrophoretic gels from which two gels designated (A,B) were called "discontinuous", and one designated (C) was described as a gel with a "stepped gradient". However, none of the above arrangements suggest a variable multilayer system of distinct electrophoretic gels, forming specific molecular sieves characterized by retention gradients for elected groups of polar biomolecules.

The above designated devices (A, B and C) only comprise two (2) layers of gels wherein the first layer serves primarily as a mechanical, and not as an analytical means (e.g., delivery of the biological sample to an analytical gel (A), or to clean the analyzed biological sample from interfering components (B), or to unspecified improvement of desired analytical procedures (C)). In addition, certain ones, called "technical" gels are composed of components which are substantially smaller, than are the main, analytical gels (A, B, C).

U.S. Pat. No. 4,306,956 to De Castro describes the first of the two-layer systems designated (A). This patent is directed to the use of thymol blue, phenol red, o-cresol red, orange G, m-cresol purple and mixtures, as a tracking dye in an SDS-PAGE electrophoresis process. The patent describes system designated (A) as follows—"Often in discontinuous sodium-dodecyl dodecyl sulfate polyacrylamide electrophoretic gels (U.S. Pat. No. 3,384,564), two separately polymerized layers of polyacrylamide, designated as 'a stacking gel' and 'a separating gel', are prepared." (Col. 1, lines 40–42). The large pore size of "the stacking gels" allows the biological sample to concentrate into narrow starting zone, necessary for good resolution in the following gel, with no change in characteristics, until it encounters a discontinuity in entering "the separating gel", either in the nature of the supporting medium, i.e., pore size, or in the buffer, e.g., pH. This change, based on entering into second gel, produces the separation of the different macromolecular species into discrete bands, but it does not relate to the present invention.

The second of the two-layer systems (B) was also called "discontinuous" by S. Moulin, J. C. Fruchart, P. Dewailly and G. Sezille—Electrophorese des lipoproteines seriques sur plaque de gel d'acrylamide-agarose, en gradient discontinu d'acrylamide. Clinca Chimica Acta, 91 (1979):159–163. The authors used two different concentrations (2% and 3%) of acrylamide and a constant concentration of agarose (0.7%). The biological samples are placed in the first gel (2%) in order to retain macromolecular components (e.g., chylomicrons), which hinder a good electrophoretic separation of other lower molecular components of diagnostic interest. However, the entire analytical separation takes place on a homogeneous second gel (3%), without any further interference of the first layer which clearly serves only as a technical preserver of the unwanted material and therefore does not relate to the present invention.

U.S. Pat. No. 4,189,370 to Boschetti describes the third of these two-layer systems (designated (C)) which was referred to as a "stepped gradient". The patent is directed to a process for preparing gels stratified upon a film, comprising two steps: first, disposing upon said film gel, being formed from a first monomer concentration and disposing upon said first film a second gel, so as to form "a discontinuous gradient" between said first gel and second gel; these layers may be spaced from polyester film and the second layer may also be disposed on said first layer. The author failed to demonstrate how the separation of biomacromolecules is enhanced by said invented separation line (between layers). However, the so claimed, but not proven "separation" may be often artificial, or otherwise incorrect, or may be related to wrongly defined fractions, etc.

The ideas of Boschetti (1980) and de Castro (1981) are basically identical, although their inventions differ in concentrations of recommended gels for electrophoresis of serum lipoproteins and/or proteins—de Castro's so called "stacking gel" has lower T % than his "separating gradient gel" offered in a wide variety of gradually increasing compositions from 0.5% to 30% T; preferred range is from about 3–27% T. Similarly, Boschetti's first gel has lower concentrations of said bi-functional allylic or acrylic compound e.g., about 7.5%, while the nongradient second gel has higher concentrations, e.g., about 10–17%, although concentrations of the monomers in the said gels differ not significantly, e.g., 2.5% and 2.0%, respectively.

However, none of the above-described methodical modifications of separating gels make possible to retain and so separate the analyzed biomolecules according to their specific retention gradients into their standard classes and subclasses. This is described in detail herein, under EXAMPLE 1 and graphically presented in FIG. II wherein a pattern obtained with de Castro's method (classified as GRAD) can be compared with the method of this inventor (classified as DISC).

U.S. Pat. No. 3,384,564 to L. Ornstein is directed to "a simultaneous separation and concentration of charged particles which may be either separately recovered or alternatively the resulting continuous thin zones of charged particles used thereafter as the starting zones with appropriate pH and/or pore size change for high resolution and further separation of the components in brief runs." (Column 1, lines 10–19) The patent states that "with a synthetic polymer like polyacrylamide, because the average pore size of a gel depends on the concentration of polymer (e.g., a 30% gel produces about a 20 Å pore and 7½% about 50), the pore size can be adjusted to the range of dimensions of the molecules to be separated" and gives the dimensions in Å and the free mobilities of a few plasma proteins at pH 8.6 (mobility unit = $10^{-5}$ cm$^2$/volt-sec.). (Column 1, line 70 –column 7, line 5).

L. Ornstein stated his basic working idea as follows: "It would appear that a 7½% aqueous polyacrylamide should exhibit extreme frictional resistance to the migration of fibrinogen, $\beta_1$ lipoprotein (and perhaps the $\alpha_2$ macroglobulin and .gamma.globulin), and that the other proteins should be able to pass through, though with substantially more difficulty than in an aqueous system. Thus differences in molecular size as well as charge can be utilized in electrophoretic separation of various components in a gel or solution of linear polymer."

L. Ornstein's claims of an electrophoresis, using three layers, although in fact only two real layers are described by him-a large pore specimen layer (it is not presently considered as a separate layer), large pore gel spacer layer (later called "stacking gel") and a small pore gel layer for further separation (=on 7.5% PAAG) of analyzed particles in a vertical cylindrical container, equipped with buffer reservoirs and electrodes, fraction elutor and sample collector. Thus, Ornstein does not relate to the present invention.

Commercially, the combination of a "stacking and separating gel" has been utilized according to de Castro by Miles Laboratories, Elkhart, Indiana, under the trademark "LipoPhor-Gels". They were primarily used for HDL-cholesterol assaying by D. Roche, V. Atger, N. T. Le Quang, A. Girard, and O. G. Edindjian in the work "Polyacrylamide Gel Electrophoresis in Quantification of High-Density Lipoprotein Cholesterol", *Clinical Chemistry*, 31/11 (1985), 1893–1985. The authors found good correlations between total HDL-cholesterol analyses and corresponding ultracentrifugal values, but never attempted to achieve the separation of HD-lipoproteins according to their molecular sizes. Their work does not interfere with this invention.

More sophisticatedly were removed from the biologic mixture of serum lipoproteins the VLDL (and chylomicrons) by the accumulation at the 5 mm thick 2%, 5% PAAG boundary, while LDL just entered the 5% PAAG. The separation between the above lipoprotein groups of VLDL and LDL thus obtained "was variable, and not sufficiently clear for analytical purposes." "The effect of the 2% and 5% gel phases was therefore to retard the LDL and VLDL over some distance of the gel system without compressing these into a thin concentrated band at a gel boundary", according to the authors J. B. Ubbing, W. J. Serfontein and L. S. deVilliers in an article "The Direct Quantification in Whole Serum of HDL Subfractions", *Clinica Chimica Acta*, 125 (1982), 165–175.

These authors achieved the above-described "stacking effect" of HDL for some kind of separation of the HDL into HDL$_2$ and HDL$_3$ subfractions, roughly corresponding to the ultra-centrifugally isolated HDL classes at the density 1.125 g/ml (HDL$_2$) and 1.21 g/ml (HDL$_3$), using an additional 3 mm thick polyacrylamide gel (PAAG), dimensions 160×120 mm, consisting of a 13% gel of classical composition at pH=8.9.

SUMMARY OF THE INVENTION

There is provided by the present invention a multilayered molecular filtration system for electrophoresis of high and very high molecular substances, such as certain proteins, lipoproteins, glycoproteins, nucleotides, etc. The filtration system of the invention comprises at least five layers arranged in a successive, discrete, discontinuous and nonsequential fashion according to partition and/or retardation coefficients for every group of assorted macromolecules to be analyzed. This makes uniquely possible the separation of molecules according to molecular weights which may differ by millions of daltons.

In one embodiment, the novel molecular sieves are employed in the form of polyacrylamide gels of different densities which are arranged into discrete discontinuous and nonsequential multilayered molecular filtration systems.

There is further disclosed by the present invention a thin substrate for electrophoretic separations of high-molecular substances, consisting of nonsequential, discrete, discontinuous and multitudinous organization of polyacrylamide gel-layers with different concentration of monomers. They may contain constant concentrations of "poring" polysaccharides, such as agaroses and/or its derivatives, or sepharoses, dextrans, etc. In optional layers, immunofixative or other material binding biological molecules can be used.

It will be readily appreciated that the multilayered filtration system for electrophoresis, microelectrophoresis or chromatographic separation in accordance with the present invention advantageously is preparable in any of practically used sizes and forms (e.g., plates, columns, capillaries, etc.), and maybe utilized for mass production.

BRIEF DESCRIPTION OF THE DRAWINGS

FIG. I illustrates examples of compositions of different multitudinous discrete sequential gel systems and discrete nonsequential multitudinous gelous molecular sieves with specific separation coefficients;

FIG. II shows a comparison between analytical potentials of discrete polyacrylamide gels with sequentially increasing concentrations versus discrete, nonsequential and multitudinous polyacrylamide-agarose gels, forming sieves with specific partition coefficients for analyzed macromolecules; and FIG. III is a schematic representation of molecular electrophoresis based on use of novel systems of discrete nonsequential multitudinous gelous molecular sieves with specific separation coefficients.

DETAILED DESCRIPTION

Figure 2:
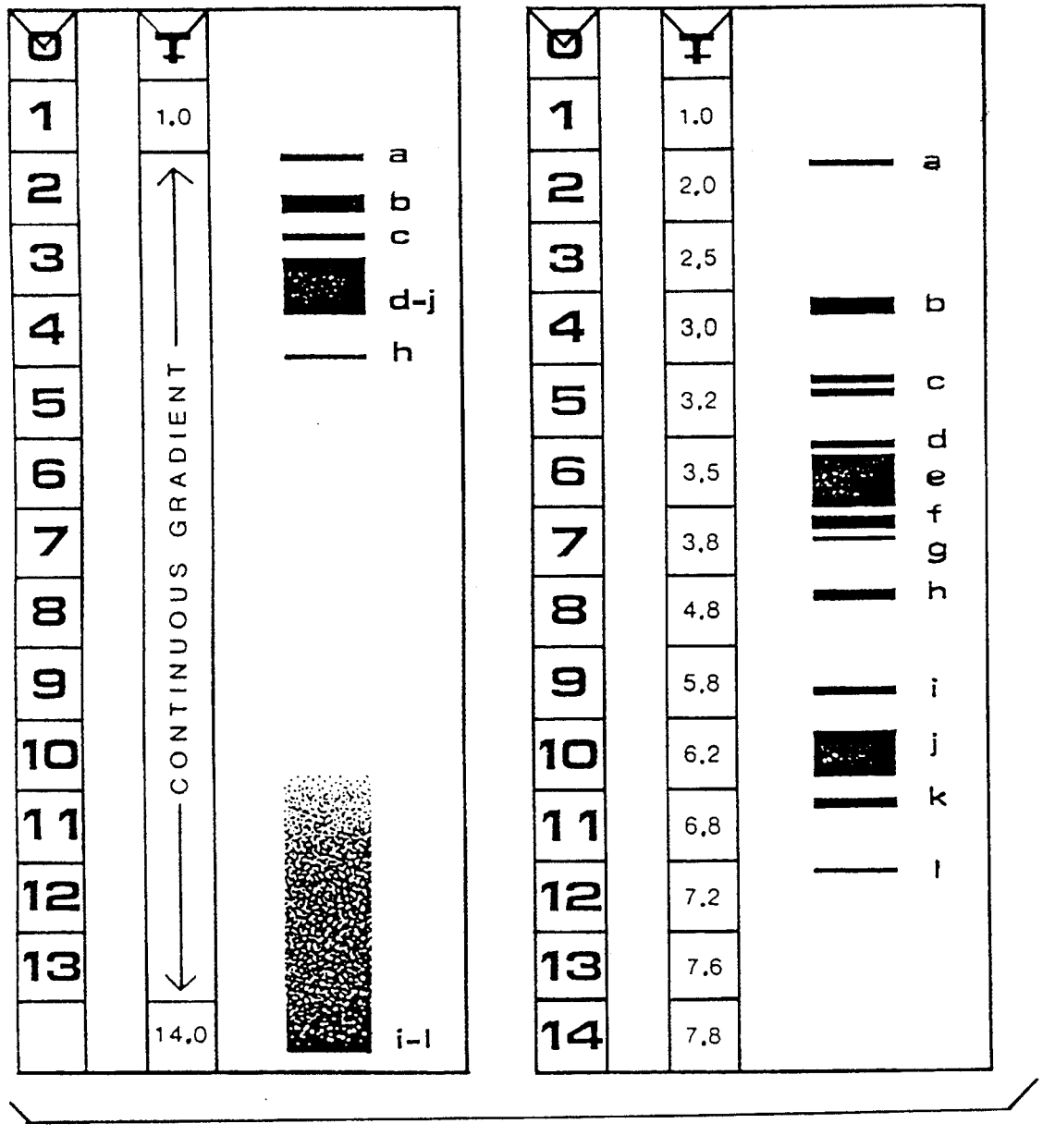
Figure 3:
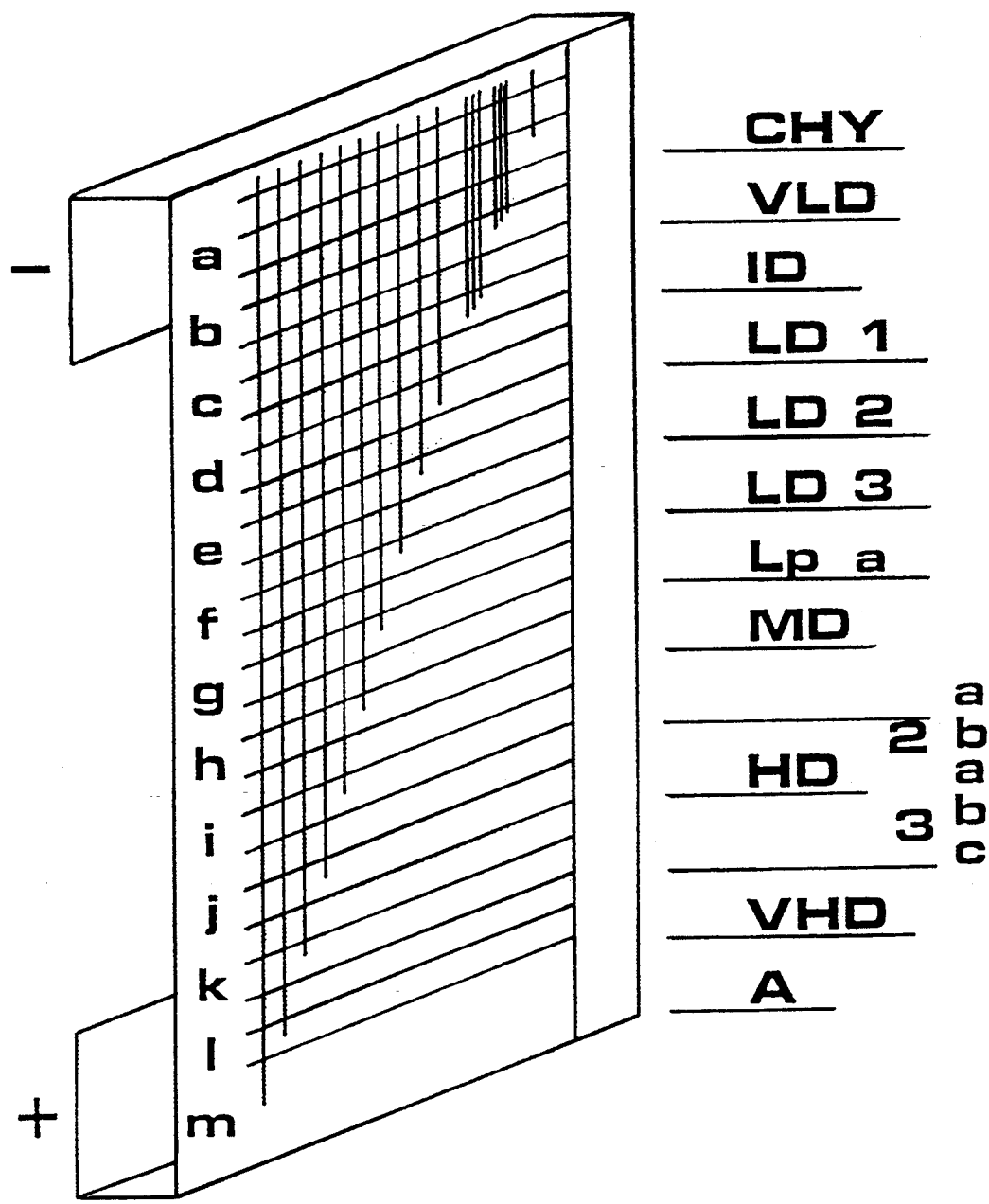

The multilayered molecular filtration systems in accordance with the invention comprise a series of at least about 5 discontinuous and nonsequential molecular sieves or separating gel-layers which are effective to separate particles according to a broad range of molecular weights when arranged in a regular or irregular, i.e., sequential or nonsequential, successions manner such that selected molecules or molecular groups are retained by the specific "binding" or sieving layers of the filtration system. The largest molecules are engaged by the first sieving layer, while all other molecules of less size pass into the next layer. The next sieve selectively keeps groups of the next large molecules, but releases the rest of the molecules of lesser size until separation of the molecular groups is completed. Optionally, the filtration system may contain a number of non-sieving or "nonbinding" layers which function to increase the resolution of the separation in certain cases.

The particles or molecules which may be separated are of various origin (synthetic or occurring in the nature) with unrestricted significance, e.g., in chemistry, pharmacology, biochemistry, pathophysiology, plant or animal physiology, or in medicine.

The separating gel layers may be prepared from all known media including, but not limited to, cellulose acetate, starch gels, agar-gels, agarose-gels, gels of agarose derivatives, polyacrylamide gels, gradient polyacrylamide gels of different gradients (e.g., from 2% to 27% of PAA and 4% to 30% of PAA), pore gradient polyacrylamide gels, mixture of, or combinations of polyacrylamide gels and different derivatives of agarose or other polysaccharides, immunofixative or biospecific sorbants, as well as any of the above gels with addition of protein-complexes-forming variants (SDS), urea, or emulators (TRITONS), or glass adhesives, etc. The gels may be solid, semifluid or fluid.

This invention is most advantageous in separations and/or determinations of molecular weights of unknown particles, or those mixtures of particles with very broad molecular sizes and weights or mixtures of very small as well as very large particles.

The object of the discrete system of layers is to filter-up, or otherwise separate macromolecular mixtures according to their molecular sizes in such a manner that each of the layers excluded (or retains, or delays) groups of molecules of higher order and releases all other molecules of lower order, e.g., of smaller molecular sizes, until the groups of the smallest molecular size are retained at the end of the mediae while none of the molecules are lost.

An optimal composition of discrete layers may be selected or developed using adequate molecular standards and/or molecular markers covering the entire molecular scale of separated mixtures or complexes.

The above specific conditions are best defined by the partition coefficient $K_D$ and by the retardation coefficient $K_R$ (designed by K. A. Ferguson: Metabolism, 13:985, 1964).

The retardation coefficient of Ferguson is given by:

$$K_R = (R+r)C$$

where $$C = (0.434\pi l')^{\frac{1}{2}}$$

where $l'$ is the length of the fiber chain per unit volume, R the radius of the partitioning molecule, and r the radius of the gel fiber.

According to the theories of gel filtration, $K_R$ should depend only on the gel structure and the size of the partitioning protein.

The partition coefficient, $K_D$, of the protein between the gel and solution, as obtained from gel filtration experiments, can be related to $K_R$, by the following relationship:

$$\log K_D = -K_R T$$

where T is a gel concentration.

If the values of $K_R$ of analyzed macromolecules are plotted against the size of radii (R) of these partitioning molecules (in Å) at a standard pH, a linear relationship is obtained (according to experience of S. Ghosh, M. K. Basu and J. Schweppe: Analytical Biochemistry, 50:592-601, 1972).

In the following text of this invention, there will be described all molecular sieves constructed in conformity with the above definitions of $K_D$ and $K_R$, called as discrete, discontinuous and nonsequential molecular sieves with specific partition and/or retardation coefficients calculated and/or experimentally proven for a specific fraction or class or subclass of analyzed complex of macromolecules.

These systems are particularly efficient in the form of discrete layers of identical length or widely varying length depending on the composition, structure, network, shape or gradation of these changes in their quality or composition. In general, there is no limit to the length of specific layers. In one embodiment, the layers are at least about 0.2 mm. In another embodiment, the layers are from about 0.5 mm to about 10 cm.

As noted above, there are at least about 5 separating gel-layers or sieving layers in the system. In one embodiment, the system comprises from about 5 to about 30 layers. Depending upon the macromolecules to be analyzed, the system will comprise, e.g., about 6–30 and, more often, about 18 gel-layers (polypeptides and/or serum proteins) with variable concentrations of copolymers in the range of from 2–30% by weight to about 2–27% by weight; about 6–18 separating gel-layers and, advantageously 12 layers (serum lipoproteins) with variable concentrations of copolymers in the range of 2–20% by weight to about 2–17% by weight; about 6–16 separating gel-layers, advantageously 8 layers (serum glyco-proteins) with variable concentrations of copolymers in the range of 3–27% by weight; about 5–20 separating gel-layers (oligonucleotides and nucleic acids and/or their fragments in the range of the size of bases to megabases) with variable concentrations of copolymers in the range of 2–30% by weight to about 5–20% by weight.

The unique discrete and discontinuous multiple arrangement of molecularly specific, e.g., specific macromolecules and/or sizes of macromolecules, retaining filters or sieves constitutes the basic principle of this invention.

For the purposes of the specification and the appended claims it will be understood that the term "discontinuous" in relation to the system of the invention is intended to mean that the specific values of T, $K_D$ and/or $K_R$ for adjacent separating gel-layers or sieves of the system will not be related in any sequential linear, exponential or logarithmic fashion, but rather, will differ by a statistically significant (for purposes of separation) nonsequential (i.e., discontinuous) value. This is clearly shown and demonstrated in both the examples and the drawing figures.

The procedure for making a discrete system of specific molecular sieves or filters includes: empiric or experimental selection between sieves and specific binders (e.g., based on immuno-affinity, complexing, physical or chemical interactions, etc.) in particular relation to the macromolecules to be isolated. Empiric or experimental selection of molecular dimensions of molecular mixtures for which the discrete system should be effective. Empiric or experimental selection of molecular standards and/or markers indicating critical margins of the dissolved molecular spectrum and preparation of discrete multitudinous systems of specific, discontinuous sieves or filters first in a working form of non-polymerized or non-gelatinized status.

The discrete gelous polymers are organized into discrete multiple layers, each of them designed to have exclusive and/or strictly specific properties, which are selectively effective in the molecular separation and/or in molecular characterization of the chosen mixture of macromolecules.

In one embodiment, the discrete layers of the gel polymers are obtained by polymerization (at elected various degrees) of recrystallized N-methylol-acrylamide with a bifunctional acrylic or allylic compound (e.g., BIS or DATD) forming a three-dimensional, cross-linked sieve of the resulting polymer having different acrylamide monomer concentrations, e.g., 36% of the acryl monomer. To activate the above reaction, a free-radical catalyst, e.g., potassium persulfate, riboflavin or TEMED, was added, as well as a sodium chloride and/or TRIS, or barbital, or similar buffer solution to provide the intended concentration of acrylamide monomer (T).

Usually, each layer is prepared individually and casted (layered) into pre-prepared glass column, capillaries, circular dishes, or pre-assembled macro- or micro-plates in the molds. Where indicated, layers containing gradients are prepared using conventional linear or exponential gradient makers (e.g., LKB-217-MULTIPHOR II, or others). Repel Silane and/or Bind Silane (LKB) may be applied, if the gels are to be bound or repelled off the glass plate.

Where needed, the above-described PAA gels may be modified and/or filled with agarose, sepharose, agarose derivatives, etc. (as demonstrated in the Examples).

The following abbreviations have the meaning indicated:
ACRYL = Acrylamide
BIS = N,N'-methylenebisacrylamide
DATD = N,N'-diallyltartardiamide
DMAPN = 3-dimethylaminopropionitrile
TEMED = N,N,N',N'-tetramethylenediamine
TRIS = tris (hydroxy-methyl) aminomethane
T = range of acrylamide monomer and bimer concentration in %

$$\% \ T = \frac{g \ ACRYL + g \ BIS}{100 \ ml \ gel} \times 100$$

PAA = polyacrylamide
PAAG = polyacrylamide gel(s)
PAAGE = polyacrylamide gel(s) electrophoresis
GPAAGE = gradient polyacrylamide gel(s) electrophoresis
C = crosslinking degree $$\% \ C = \frac{g \ BIS}{g \ ACRYL + g \ BIS} \times 100$$

Where suitable, the layers are filled starting from the bottom of the molds. The "stacking gels" are layered as the last layer.

At the end of this operation, any known techniques can be employed for the construction of the applicator gels with precast sample wells (capable of absorbing from 5 $\mu$l to 80 $\mu$l sample volumes).

Construction of the final system of specific layers is prepared in any quantity, quality, physical form, composition and sequence. The borderlines of the layers may be constructed with sharp, visible edges (for example if the previous layer is fully gelatinized, when the following one is being overlaid) or in unbroken confluent fashion.

Semiliquid or liquid gelous forms which do not change their physical status in time, although fully polymerized, have to be fitted into their containers (of any shape) in order to prevent a mixing of materials.

The separation lines of the above layers (of the same, or different concentrations and/or compositions) are rectilinear when electrophoretic plates or columns are elected or strictly circular (when circular microelectrophosis, or circular diffusion techniques are picked-up).

All possible mixtures of gelatinizing materials, with or without any additional "filling" gels, can be used without restrictions.

The discrete layers may be particularly efficient as system of almost identical or widely varying layers, because of their optimal composition, structure or length or shape or gradation of changes in their quality or composition.

The final shape of these discrete systems of molecular sieves may be manufactured in any thickness and usable forms in large or small (e.g. microplates) plates with glasseous or plastic supports, columns in glass tubes, or in capillaries, chromatographic columns, etc.

In this way, gel-plates of various sizes (from 125×250 mm, allowing the simultaneous separation of up to 96 biological samples—down to 50×50 mm, allowing the simultaneous separation of 9 samples and only one standard) may be prepared.

The preservation of gels in glass plates, containing analytical systems of discrete and/or discontinuous gelose layers may be preserved by immersion into a buffer solution as well as by packing them in storage bags. In such manner, it will be possible to handle their shipment and other usual commercial handling.

The above-described gel-casting forms (e.g. plates, tubes, capillaries, etc.) should be useful with any known electrophoretic procedure.

The optimal composition of the multitudinous, discrete, nonsequential gel layers may be prepared or developed by determination of partition ($K_D$) and/or retardation ($K_R$) coefficients, calculated for the selected molecular groups of the analyzed mixture.

All known forms of low or high voltage (vertical, horizontal, radial, capillary, etc.) electrophoresis, electrofocussing, chromatography, etc. may be utilized for separation of macromolecules. The mode of distribution of mixed macromolecules throughout the mediae may also be strongly dependable on the available instrumentation. However, once the best fitting instrumentation is established, it may be easily standardized. Specific electrophoretic mA, V, V-hrs. (buffer strength, pH continuity, discontinuity, etc.) have to be established. For the separation of genetic material a Pulse Field Electrophoresis may also be employed.

The unique discrete and discontinuous nonsequential and multitudinous arrangement of molecularly specific (e.g. specific for certain macromolecules and/or sizes of macromolecules) molecular filters or sieves constructed in agreement with separation coefficients, constitutes the basic principle of this invention.

FIG. I depicts compositions of discrete sequential (A,B) and discrete nonsequential (C–I) systems of different molecular sieves, comprising from layers (1–14) of copolymers of acrylamide gels, wherein each individual layer differs from the adjacent layer.

Number "0" is assigned to the "sampling" or "stocking gel" equipped with sample holes.

Letter "T" indicates % T, e.g. range of acrylamide comonomers concentration in percent, utilized in gels (represented in that particular column).

Letters A–I characterize system of gels, sampled in each column, every layer concentration different from each other.

Shaded fields in the said columns F-1 represent into PAA filled materials:
  column F=agarose with or without distantly layers
  column G=linear gradient PAAG
  column H=different discrete non-sequential PAAG with their distantly layers
  column I=with a layer of immunofixative material.

FIG. II demonstrates a natural polydispersed macromolecular system (e.g., pre-isolated serum lipoproteins by ultracentrifugation) separates into 5–6 groups (=fractions) on discrete polyacrylamide gels with sequentially increasing concentrations, but into 12–13 groups and subgroups (classes and subclasses) on the discrete, nonsequential and multitudinous agarose-polyacrylamide gels, forming sieves with specific partition coefficients for their classes and most important subclasses.

Number "0" is assigned to the "sampling" gels, equipped with sample holes.

Numbers 1–14 indicate amount of layers.

Letter "T" indicates % T, e.g., range of acrylamide monomers concentration in percent, utilized in particular gels.

Abbreviation "GRAD" accounts for discrete polyacrylamide gels with sequentially increasing concentrations.

Abbreviations "DISC" accounts for a discrete, nonsequential, discontinuous and multitudinous polyacrylamide-agarose gels, forming sieves with specific partition coefficients for lipoproteins.

Letters A–I represent related individual groups and/or subgroups of the identical molecular system, separated for a comparison on "GRAD" and "DISC" analytical systems. The superiority of the analytical potential of the "DISC" system is clearly documented.

FIG. III depicts a glass plate in homogeneous electric field with adhering system of discrete nonsequential gelous molecular sieves, build according to the methods described under EXAMPLE 7, in compliance with partition ($K_D$) and retardation ($K_R$) coefficients for analyzed lipoprotein classes and diagnostically important subclasses.

The separating layers (empty intervals) alternate with distantly layers (shaded intervals).

Alphabetically arranged set of the letters (to the left) correspond to the letters used for characterizing individual classes and subclasses of serum lipoproteins described under EXAMPLE 7. They are related to standard abbreviations of the lipoprotein classes and subclasses (to the right).

The following nonlimiting examples may contribute to the more clear understanding of the present invention.

EXAMPLES

The following examples illustrate the use of the system of molecular sieves with specific retention gradients described in this invention.

EXAMPLE 1

The organization of discrete molecular sieves with sequentially increasing concentration of the copolymer has no different sieving effect than have the corresponding well known "gradient gels" as it depicted on FIG. I, column A[1].

[1] All examples (1–9) refer to the FIG. I.
Number "0" is assigned to the "sampling" or "stacking gel", equipped with sample holes. Letter "T" indicates % T, e.g., range of acrylamide comonomers concentration in percent, utilized in gels (represented in that particular column).
Letters A–I characterize gels, sampled in each column, different from each other.

For example, the polyacrylamide gels arranged into discrete, but sequential order like into a system of gels of sequential concentrations from 1%, 2%, 3%, 4% 5%, 6%, 7%, 8%, 9%, 10%, 11%, 12%, 13%, 14%, have been used.

The gel mixture for each layer of gel is prepared separately. For the preparation of individual gel layers was provided a basic solution which contained 1.6 ml of TRIS-borate $Na_2$ EDTA (TBE) buffer (pH=8.3) 1.0 ml of 6.4% 3-dimethylaminopropionitrile (DMAPN) and 4.25 ml of a acrylamide-bisacrylamide solution which concentration corresponded to those, defined for the given gel-layer on FIG. I, column A. Distilled and deionized water is added to each gel mixture, in order to adjust the total volume to 15.0 ml.

0.5 ml of 1.6% ammonium persulfate is added to each of the gel mixtures, so that the speed of the transfer to the gel mould is quick. The components are mixed and the selected portion (1.0 ml) is carried over into the casting form, but not before the previous layer has gelified.

The TBE buffer solution was prepared from 32.7078 g of TRIS, 14.8392 g of boric acid and 3.35025 g of $Na_2$ EDTA, dissolved in 3,000 ml of deionized water, after adjustment to the pH 8.3 with 2N HCl. The 6.4% DMAPN solution was prepared by resolving 16 ml of concentrated DMAPN in 250 ml of deionized water. The acrylamide-bisacrylamide solution was prepared by adding 47.5 g acrylamide to 2.5 g N,N'-methylenebisacrylamide in 250 ml of deionized water. The ammonium persulfate solution was prepared by adding 1.6 g ammonium persulfate in 100 ml of deionized water. (All chemicals were obtained from Sigma Chemicals).

The serum lipoproteins were pre-isolated by ultracentrifugation at density 1.21 g/ml, adjusted by NaCl and KBr, using Beckman Model L Ultracentrifuge at 100 000 g for 16 hours in a Beckman type 50 rotor.

The electrophoresis of lipoprotein flotants and molecular weight standards was performed in a 10 cm long, 10 cm large and 2.0 mm thick vertical slab gels (casted in GSC-8 apparatus) at 14° C. for the period of 16 hours, 1 hour at 30 V and 15 hours at constant voltage of 125 V, in TBE buffer (pH=8.3), utilizing Pharmacia-Uppsala analytical vertical system (GE-2/4-LS cell).

The lipoproteins separated in gels were prestained (by mixing of equal volume of florant with 5 g per L solution of Sudan Black B in ethylene glycol), or stained after a standard fixation (200 g trichloracetic acid in 1000 ml of distilled water) with Coomassie Blue G 250 for apolipoproteins (in a mixture of equal portions of acid copper sulfate solution and solved Coomassie Blue in diluted methanol), or Sudan Black B for lipidic moiety (using SBB in ethyleneglycol or in 60% ethanol), respectively Oil red O stain. The gels were thereafter destained and preserved in adequate preserving solution, or dried.

There were also employed molecular weight standards: Carboxylated Latex Beads of molecular weight 5,388,333 d (DOW Chemicals), Thyreoglobulin dimer of molecular weight 1,400,000 d(Phamacia) and Thyreoglobulin monomer of molecular weight 669,000 d (Pharmacia), with Ferritin of molecular weight 440,000 d (Sigma, Chemical Company), Catalase of molecular weight 230,000 d (Behringer Mannheim), Aldolase (isolated from muscle) of molecular weight 158,000 d (Calbiochem), and Bovine serum albumin of molecular weight 66,250 d (Pharmacia). The results, obtained by the separation of serum lipoproteins on the above-described discrete polyacrylamide gel layers with sequentially increasing concentrations (demonstrated from T=1%, 2%, 3%, 4%, 5%, 6%, 7%, 8%, 9%, 10%, 11%, 12%, 13%, 14%) to 16% or even 27%, respectively were really not more successful, than it has been previously experienced using for example 1% or 1.2% agarose gels.

The serum lipoprotein separated into the following fractions (see FIG. II, column GRAD):

a=contains chylomicrons (CHY) and their fragments (VVLDL),
b=contains very low-density lipoproteins (VLDL),
c–j=complex of unseparated lipoprotein classes and subclasses of low density lipoprotein group (LDL),
h=consists most probably from a medium density lipoprotein (MDL), and
i–l=complex of unseparated lipoprotein group of high-density lipoproteins (HDL), characterized by a long, trailing fraction.

The insufficiency of the discrete polyacrylamide gels with sequentially increased concentrations separation of serum lipoproteins was evidently demonstrated.

EXAMPLE 2

An analytical system of eleven discrete polyacrylamide gels with sequentially increasing concentrations was prepared according to the method given in EXAMPLE 1, as delineated on FIG. I, column B. However, the original layer numbers 3–5 were substituted with one longer gel layer characterized by T=3% and layer numbers 7–9 by an another longer layer of T=5%. More spacious gel layers with critical concentrations of T=3% and T=5% offered significantly better separation of biomacromolecules of molecular weight ranging from 4–2,000,000 d and from 800,000–1,300,000 daltons.

This gel system was also further technically adjusted so that between layer numbers 2 and 3, as well as 3 and 4, 4 and 5, 5 and 6, 6 and 7, 7 and 8, 8 and 9 and finally 9 and 10 were inserted standard gel layers of a standard concentration of co-monomers expressed by T=2.5%.

In this manner, the resolution potential of the above-described system was significantly enhanced.

EXAMPLE 3

An analytical system of twelve discrete polyacrylamide gels with nonsequentially increased concentrations of co-monomers was prepared according to the method given in EXAMPLE 1, as illustrate on FIG. I, column C with the extraordinary arrangement that the differences in the concentration of comonomers were decreased to 0.2% T in the upper part of the system. To the contrary, the following gel layer, characterized T=3% was three times lengthened in order to facilitate better separation of biomacromolecules of molecular weight ranging from 10,000,000–2,500,000 daltons. The lower part of system was arranged into a so called nonsequential form of gels characterized by nonsequential increasing concentrations of co-monomers, expressed by nonsequential values of the index T %.

The above introduced discrete gelose sieves possess distinguished and very specific composition, symbolized by independently irregular, but relatable specific indexes T %. They were intentionally prepared in the way to meet specific conditions, under which the density of their network will selectively allow the proper partition and retardation of intended biomacromolecules.

EXAMPLE 4

A system of discrete, multitudinous, nonsequential gelous molecular sieves was prepared according to the design placed into column D, FIG. I and methods given in EXAMPLE 1. The specificity of this arrangement is based on an insertion of a polyacrylamide gradient gel-plate with linearly increasing concentration from 4 to 6% T into the position 8–11.

This assortment allowed an improved separation of biomacromolecules in the range of 800,000–1,500,000 daltons.

EXAMPLE 5

For the successful separation of viral components and their fragments was prepared a system of discrete, multitudinous, nonsequential gelous molecular sieves according to the design of column E, FIG. I and methods, given in EXAMPLE 1.

The gel-layer numbers 2 and 3 were substituted with a gradient polyacrylamide gel with linearly increasing concentration of co-monomers from T=2% to T=3%. Similarly the gel-layer numbers 8–10 were replaced with gradient polyacrylamide gels of exponentially increasing concentration from 4–5.8% T.

The above-described set of changes made possible that biomolecules of molecular weights in range of 30,000,000–10,000,000 daltons and in the range of 500,000–1,000,000 daltons separated in a nonstandard manner, some of them more clearly.

Discrete or nondiscrete (e.g. continual), but sequential polyacrylamide gradient gels may replace any segment in a system of discrete, nonsequential, multitudinous gels, so far they contribute to the improvement in separation of analyzed biomacromolecules. Their sequence may be adjusted linearly, or exponentially. Their length may be variable. Any gelatinizing material may be employed.

EXAMPLE 6

A system of multitudinous, discrete, nonsequential polyacrylamide gels, in part forming sieves with specific partition coefficients for analyzed macromolecules was prepared according to the plan given in column G, FIG. I with the exception of the layer numbers 4–7, where an another layer of a linear gradient 3.0–4.8% T polyacrylamide gel was inserted.

Although the above-described analytical system provides remarkably good separation of the pre-isolated serum lipoproteins for their classes without the insertion of the 3.0–4.8% T layer of the linear polyacrylamide gel (GPAAG), the GPAAG itself eliminates[2] the superior capability of the system of molecular sieves selected according to the $K_D$ and/or $K_R$ of individual classes of serum lipoproteins.
[2]See FIG. II, column GRAD, lipoprotein group d–j.

The group of intermediate (IDL) and specifically low-density lipoproteins (LDL)[3] failed to separate into three subclasses: $LDL_1$, $LDL_2$ and $LDL_3$. To the contrary, the group of very high-density
[3]See FIG. II, column DISC, lipoprotein group d–g. lipoproteins (HDL) separated into known subclasses. An another proof of selective action of GPAAG.
[3]See FIG. II, column DISC, lipoprotein group d–g.

EXAMPLE 7

Particularly for the separation of serum lipoproteins a combined agarose-polyacrylamide system of multitudinous, discrete, nonsequential molecular sieves was assembled according to a design presented in column F, FIG. I. The concentrations of the copolymers in individual gel-layers were adjusted according to the appropriate $K_D$ and/or $K_R$ in a mode which made possible to separate diagnostically important classes and subclasses of lipoproteins of low, intermediate and high molecular weight in one analytical system.

The gel mixture for each layer of gel is prepared separately. A basic solution was provided, which contained 1.6 ml of TRIS-Borate-$Na_2$ EDTA (TBE) buffer (pH=8.3), 1.0 ml of 6.4% 3-dimethylaminopropionitrile (DMAPN) later replaced with TEMED (N,N,N',N',-tetramethylenediamine) and 3.9 ml of 2% agarose (or in some experiments of Sepharose 2B, or 4B, or 6B), plus 4.25 ml of an acrylamide plus bisacrylamide solution which concentration corresponded to those, designed for the given gel-layer on FIG I, column F. Distilled and deionized water is added to each gel mixture, in order to adjust the total volume to 15.0 ml.

All the above-described gel-mixtures are kept hot in a water-bath up to 90° C., so that the agarose remained soluble. Before the use of the above mixture for a preparation of corresponding gel-layer, the mixture is removed from the water-bath and let cool to 50°–55° C. 0.5 ml of 1.6% ammonium persulfate is added to each of the gel mixtures, so that the speed of the transfer to the gel mould is quick. The components are mixed and the selected portion (for example 1.0 ml) is carried over into the casting form, but not before the previous layer gelatinized.

Most of the reagents and/or solutions were prepared according to the recipes given under EXAMPLE 1. The 2% agarose was prepared according to the following specifications: 2 g of Seakem agarose (Marine Colloids, Inc.) was dispersed into 90 ml of deionized, 70° C. hot distilled water, cooled to 50°–55° C., adjusted to 100 ml and used, or stored at 4° C.

Serum lipoproteins were pre-isolated, as described under EXAMPLE 1.

Their electrophoresis, fixation, staining, destaining, preserving and drying was described under EXAMPLE 1.

The molecular weight standards, used always during separations of biomacromolecules were also described previously.

There is no restriction concerning the composition of the basic gelous matrix, not the selection or composition, or concentration (0.5% agarose concentration was mostly used in this invention) of the filling material. This invention is not restricted to polyacrylamide gels used here only for an example. Any net forming and well netting material, resembling durable and well consistent gels may be employed for construction of discrete, multitudinous, nonsequential gels in order to construct molecular sieves with specific $K_D$ and/or $K_R$ for separations of intended groups or mixtures of biomacromolecules.

The above analytical gelose systems were prepared also as a thin (=1.0 mm), or ultra-thin (=0.5 mm) gels and as well as so called "micro" gels (5.0×5.0 cm). The thinner modifications offered better separation of lipoprotein subclasses, mainly in the group of HDL. Similarly, the formation of electrophoretic zones was improved.

The serum lipoproteins were separated into the classes and subclasses which were verified by their identification with corresponding classes and subclasses isolated by preparative ultracentrifugation at specific densities and by a reanalysis using analytical micro-ultracentrifugation, as well as by laser—light scattering spectroscopy and finally by immunochemical and chemical analyses.

The following separation of serum lipoproteins was achieved:

1. The first very thin and porous gel-layer (of 1.0–1.5 % T) separates out only the largest molecules (e.g. 1,000–4,000 Å[4], e.g., 100,000,000 d[5] to 350,000,000 d molecular weight), representing exogenous chylomicrons (CHY). Usually, they constitute fraction "a" (FIG. II, column DISC), or its pre-fraction, if their concentration is extremely high.
[4]Å=Angstrom=$10^8$ cm
[5]d=dalton=a unit of molecular weight.

The levels of chylomicrons (0.05–0.1 mg %) are in human circulation so low in the fasting stage that they become inseparable from endogenous chylomicrons and/or from their fragments. In this case, only one fraction appears in the T=2% molecular sieve.

2. The second gel-layer (of 2.0% T) is characterized by $K_R$, mostly suitable to retard chylomicrons of hepatic origin of smaller particle size (600–900 Å). Under physiological conditions, even the next group of lipoproteins (VVDL) may be separated in this molecular sieve.

3. The third gel-layer (of 2.5% T) retains the chylomicron fragments, or very very low-density lipoproteins (VVLDL), characterized by a range of sizes (550–450 Å) and molecular weights (approx. 80,000,000–25,000,000 daltons). Similarly, under physiologic condition, even this class may contribute to the fraction "a", FIG II.

4. The forth layer (of 3.0% T) represents the specific molecular sieve with retardation coefficient for VLDL (=very-low density lipoproteins), forming few subclasses in the broad range of 600 to 400 Å, e.g. in the range of 18,000,000–6,000,000 d (mean 12,000,000 d). Under physiologic conditions, this class has only one, but may reveal up to four subclasses in pathologic stages. Fraction b.

5. The fifth layer (of T=3.2 (+)0.1%) has to fit for the retardation coefficient for IDL (= intermediate density chylomicrons), diagnostically second most important class in the spectrum of serum lipoproteins. It may belong metabolically to VLDL, but separates on the invented systems of gels well, producing up to 2–4 subclasses under pathologic conditions in the range of sizes 350–250 Å and molecular weights of 5,000,000–4,500,000 daltons. Inter-layers of standard network of T=2% enhances the clarity of separation. Fraction c.

6. The sixth cluster of layers (in fact a group of layers ranging in their netting from T=3.5–4.5%, eventually combined with interlayers of standard network of T=2%) is equipped with retardation coefficients $K_R$, fitting for retardation of all LDL (=low density lipoprotein class) subclasses. The undivided LDL class includes lipoprotein particles with sizes ranging from 260–210 Å and molecular weights from 4,000,000–1,500,000 d. Under physiological, as well as pathological conditions are separable three standard subclasses, using the analytical system described in this invention: $LDL_1$ (particle size $\phi$ 260 Å, and $\phi$ m.w. 3,500,000 d), $LDL_2$ (particle size $\phi$ 225 Å, and $\phi$ m.w. 2,500,000 d) and $LDL_3$ (particle size $\phi$ 210 Å, and m.w. 1,600,000 d). Two specific densities of nettings (T=3.5% and 3.8%), or even better five densities of nettings (T=3.3% 3.5% 3.7%, 3.9% and 4.1%) are utilized. Complex d–g.

7. The seventh layer (of T=4.8% ±0.2%) is adequate for $K_R$ of MDL (=medium density lipoprotein), whereby also $K_R$ and a proper density of netting may be calculated for Lp(a) if desired. The MDL render particles of size 200–190 Å and of m.w. 1,000,000–900,000 d and mean density 1.076 g/ml. Fraction h.

8. The eighth cluster of selective layers, eventually with combination of intermediate, alternating standard layers, offers the separation of the complicated HDL class. There is some confusion in the present nomenclature, however. Therefore, the minimal physical parameters have to be given in order to correctly describe, which subclasses are in fact determined of HDL (d 1.0635–1.210 g/ml).[6]

[6]In consent with D. W. Anderson, A. V. Nichols, S. S. Pan and F. T. Lindgren: Atherosclerosis, 29, 161–179, 1978.

The $HDL_1$=2b (d 1.070–1.100 g/ml) represents a less known lipoprotein class. Protein content 25%. Mean banding position 1.090 g/ml. M.W.=4,200,000±200,000. Peak $F·_{1.21}$ rate 5.40±0.30.

The $HDL_2$=2a (d 1.100–1.125 g/ml) includes lipoprotein in the size range 160–140 Å. Cholesterol: protein ratio 0.50 to 0.40. Protein content 52%. Mean banding position 1.110 g/ml. M.W.=2,630,000 ±100,000. Peak $F·_{1.21}$ rate 3.15±0.06.

The $HDL_3$=3 a–c (d 1.125–1.200 g/ml) represents a lipoprotein of size range from 113–115 Å. Cholesterol: protein ratio 0.37–0.14. Protein content 68%. Mean banding position 1.145 g/ml. M.W.=1,770,000±90,000. Peak $F·_{1.21}$ rate 1.56±0.13.

The $VHDL_1$ (mean d <1.250 g/ml), protein content $\phi/80\%$
The $VHDL_2$ (mean d >1.250 g/ml), protein content The VVHDL (mean banding position 1.342 g/ml), protein content 98%. Complex i–l.

The system of molecular sieves consisting from polyacrylamide gels was calculated from corresponding $K_D$ and $K_R$ for $HDL_1$ (T=5.0%), $HDL_2$ (T=11.6%), $HDL_3$ (T=16.3%) and VHDL (T=18.0%). With the polyacrylamideagarose gels we experienced adequate separation of the above subclasses in the gelous sieves of the range of 5.0–8.0% T, mainly after shorter electrophoretic runs. One of such separations is depicted on FIG. II, column "DISC", fractions "i–l". (Letters "A–I" represent related individual groups and/or subgroups of the identical molecular system, separated for a comparison on "GRAD" and "DISC" analytical systems).

The superiority of the analytical potential of the "DISC" system is clearly documented.

EXAMPLE 8

A combined agarose-polyacrylamide system of multitudinous, discrete, nonsequential molecular sieves was constructed according to the design presented in column H, FIG. I.

Similarly, as in the previous case, the concentrations of the copolymers in individual gel-layers were adjusted according to the appropriate $K_D$ and/or $K_R$ in a mode which made possible to separate diagnostically important classes and subclasses of lipoproteins of low, intermediate and high molecular weight in one analytical system.

The method of preparation of such gels was given under EXAMPLE 7 and 1 with the specification that layer number 11 was replaced with 11.6% T polyacrylamide gel, number 12 with a similar 16.3% T PAA gel and number 13 with 18.0% T PAA gel.

The above-described modification allowed to separate better the subclasses of HDL: $HDL_1$–$HDL_2$–$HDL_3$.

Combinations of plain polyacrylamide gels and those filled with agarose or its derivatives may be utilized, whenever indicated.

The sequential, continuous gradients may be placed anywhere into the analytical system of nonsequential, discontinuous layers. They may be linear, or exponential.

The length of the said continuous gradients may be variable and so may be the material, from which the said matrixes may be prepared.

The optimal "filling matrix material" constitutes, for example, of an agarose and/or it derivatives, wherein any of the substituents are attached to the agarose molecule via: a hydroxyl linkage, or an ester linkage, or an ether linkage, or an amide linkage, or an amine linkage, or an isourea linkage, or a carbamate linkage.

For example, the layer number 14 was replaced in the standard agarose-polyacrylamide gel system of multitudinous, discrete, nonsequential molecular sieves, made according to the project given in the column F, FIG. I.

The replacement of agarose was made in the same manner with a hydrophobic agarose derivative, the ω-aminohexyl-Sepharose 4B (e.g. 1,6-diaminohexanesepharose, attached through the amino-group to Sepharose 4B). It contained 6–1 μ moles of 1.6 diaminohexane per ml gel (Sigma, Chemical Company). The 2% derivative of Sepharose 4B was prepared according to the following specifications: 0.2 g of ω-aminohexyl-Sepharose 4B was dissolved in 9.0 ml of distilled water, heated to 70° C., cooled to 50°–55° C., adjusted to 10.0 ml with deionized water, cooled and stored in form of a gel at 4° C.

In the above arrangement, the last molecular sieve possessed the function of a affinity chromatography medium. The length of the sieve may be adapted accordingly.

EXAMPLE 9

The above-described combination of discrete, discontinuous, nonsequential system of multilayered molecular sieves, formed either from homogeneous or nonhomogeneous substances, may be further combined with remarkable effectiveness with a specific layer, containing immunofixative material, if there is a need for a selective isolation of a chosen component from an analyzed molecular spectrum (see column I of FIG. I).

The said specific layer with immunofixative capabilities has to be equipped with nonfiltrating, non-sieving properties, e.g., releasing particular molecular groups, passing through this matrix.

Only one selected protein, against which the matrix contains specific antibodies, would be precipitated during the primary process of separation of the entire molecular spectrum.

For example, the Lp(a) was routinely retained during regular analytical process, the protein-immuno-complex was eluted from the above specific matrix and the atherogenic lipoprotein Lp(a) was separated out for further physicochemical studies.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A system of multilayered, discrete, discontinuous, nonsequential gels for molecular electrophoresis of biologic particles and macromolecules, comprising at least about five discrete separating gel-layers, wherein each gelous layer is defined by specific separation coefficients represented by $K_D$ and $K_R$ for the analyzed group of molecules, which direct the concentration of the medium and density of netting of each gelous layer, and wherein the value of $K_D$ and $K_R$ for each discrete separating gel layer differs from an adjacent layer by a significant discontinuous and nonsequential value and wherein one or more distinct intermediate gelous layers having a concentration of acrylamide polymer, ranging in amounts from about 1.5% to 2.5% T are inserted between the separating gels.

* * * * *